US008349366B2

(12) United States Patent
Remon et al.

(10) Patent No.: US 8,349,366 B2
(45) Date of Patent: *Jan. 8, 2013

(54) IMMEDIATE RELEASE PHARMACEUTICAL GRANULE COMPOSITIONS AND A CONTINUOUS PROCESS FOR MAKING THEM

(75) Inventors: Jean Paul Remon, Melle (BE); Chris Vervaet, Kachtem (BE)

(73) Assignee: Universiteit Gent, Ghent (BE)

( * ) Notice: Subject to any disclaimer, the term of this patent is extended or adjusted under 35 U.S.C. 154(b) by 130 days.

This patent is subject to a terminal disclaimer.

(21) Appl. No.: 12/815,715

(22) Filed: Jun. 15, 2010

(65) Prior Publication Data

US 2011/0027377 A1  Feb. 3, 2011

Related U.S. Application Data

(63) Continuation of application No. 11/276,577, filed on Mar. 6, 2006, now abandoned, which is a continuation-in-part of application No. 10/933,674, filed on Sep. 3, 2004, now abandoned, which is a continuation-in-part of application No. PCT/BE03/00040, filed on Mar. 5, 2003.

(30) Foreign Application Priority Data

Mar. 6, 2002  (GB) ................................. 0205253.8

(51) Int. Cl.
*A61K 9/14* (2006.01)
(52) U.S. Cl. ...................................................... 424/489
(58) Field of Classification Search .................. None
See application file for complete search history.

(56) References Cited

U.S. PATENT DOCUMENTS

| | | | |
|---|---|---|---|
| 3,639,637 A | 2/1972 | Campbell | |
| 4,235,892 A | 11/1980 | Nagabhushan | |
| 4,603,123 A | 7/1986 | Chiesi | |
| 4,762,702 A | 8/1988 | Gergely et al. | |
| 4,880,623 A | 11/1989 | Piergiorgio et al. | |
| 4,935,531 A * | 6/1990 | Ward et al. | 549/264 |
| 5,082,863 A * | 1/1992 | Apelian et al. | 514/618 |
| 5,362,860 A | 11/1994 | Huang et al. | |
| 5,476,654 A | 12/1995 | Conte et al. | |
| 5,646,131 A | 7/1997 | Badwan et al. | |
| 6,010,719 A | 1/2000 | Remon et al. | |
| 6,153,206 A | 11/2000 | Anton et al. | |
| 6,211,185 B1 | 4/2001 | Strobel et al. | |
| 6,368,634 B1 | 4/2002 | Remon | |
| 6,550,955 B2 | 4/2003 | D'Silva | |
| 2001/0044409 A1 | 11/2001 | Ghebre-Sellassie et al. | |
| 2001/0046526 A1 * | 11/2001 | Greenfelder | 424/779 |
| 2001/0048946 A1 | 12/2001 | Ghebre-Sellassie | |
| 2002/0150620 A1 | 10/2002 | Namburi et al. | |
| 2003/0224043 A1 * | 12/2003 | Appel et al. | 424/465 |
| 2005/0058705 A1 | 3/2005 | Remon et al. | |
| 2007/0009592 A1 | 1/2007 | Remon et al. | |

FOREIGN PATENT DOCUMENTS

| | | |
|---|---|---|
| EP | 0 352 190 B1 | 11/1992 |
| EP | 0 403 383 B1 | 8/1994 |
| WO | WO 94/23700 A1 | 10/1994 |
| WO | WO 9423700 A1 * | 10/1994 |
| WO | WO 99/12524 A1 | 3/1999 |
| WO | WO 02/17877 A2 | 3/2002 |
| WO | WO 03/074031 A1 | 9/2003 |

OTHER PUBLICATIONS

U.S. Appl. No. 10/933,674, filed Sep. 3, 2004, Remon et al.
U.S. Appl. No. 11/276,577, filed Mar. 6, 2006, Remon et al.
U.S. Appl. No. 12/815,781, filed Jun. 15, 2010, Remon et al.
Advisory Action for U.S. Appl. No. 10/933,674, dated Sep. 29, 2008.
Advisory Action for U.S. Appl. No. 11/276,577, Sep. 29, 2008.
Advisory Action for U.S. Appl. No. 10/933,674, dated Oct. 23, 2009.
Advisory Action for U.S. Appl. No. 11/276,577, dated Oct. 23, 2009.
Advisory Action for U.S. Appl. No. 11/276,577, dated May 5, 2010.
Advisory Action for U.S. Appl. No. 10/933,674, dated May 6, 2010.
Amidon et al., "A Theoretical Basis for a Biopharmaceutic Drug Classification: The Correlation of in Vitro Drug Product Dissolution and in Vivo bioavailability," *Pharm. Res.* 12(3):413-420 (1995).
Elbers et al., "Effect of amount and composition of granulation liquid on mixing, extrusion and spheronization," *Drug Development and Industrial Pharmacy* 18(5):501-517 (1992).
Examination Report for Pakistani Patent Application No. 544/2010, received Oct. 19, 2010.
English Translation of Luomingsheng, Gaotianhui, *Medicament Adjuvant Dictionary*, publishing press of science and technology of SiChuang: 16-22, 504-511 (1995).
English Translation of Office Action for Chinese Patent Application No. 03805386.1, dispatched Dec. 18, 2009.
English Translation of Office Action for Chinese Patent Application No. 03805386.1, dispatched Jul. 3, 2009.
English Translation of Office Action for Korean Patent Application No. 10-2004-7013775, dated Feb. 25, 2010.
English Translation of Office Action for Polish Patent Application No. P 372579, dated Sep. 9, 2009.

(Continued)

*Primary Examiner* — Susan Tran
(74) *Attorney, Agent, or Firm* — Clark & Elbing LLP

(57) ABSTRACT

A pharmaceutical or veterinary granule composition in the form of a mixture consisting essentially of: (i) at least one drug classifiable as Class II or Class IV of the Biopharmaceutical Classification System, wherein said drug (i) constitutes from above about 20% to 50% by weight of the composition, said pharmaceutical or veterinary granule composition providing a drug release of at least 70% within 10 minutes in water, (ii) a first excipient being a maltodextrin representing from 40% by weight to 85% by weight of said composition, (iii) a wetting amount of a second excipient being a polyethylene glycol having a weight number molecular weight between 300 and 5,000, said second excipient comprising a solid fraction and a liquid fraction, and representing from 15% to 40% by weight of said composition, and optionally one or more pharma-ceutically acceptable fillers selected from the group consisting of hydrocolloids, glidants, lubricants, surfactants and diluents, wherein the weight ratio of said first excipient (ii) to said second excipient (iii) is in a range from 1:1 to 5:1.

7 Claims, 7 Drawing Sheets

OTHER PUBLICATIONS

English Translation of Office Action for Polish Patent Application No. P 372579, dated Mar. 31, 2010.
English Translation of Office Action for Polish Patent Application No. P 372579, dated Jan. 18, 2010.
English Translation of Search Report of Taiwan Patent Application No. 92104481 (date of completion of the search: May 14, 2007).
Examination Report for Pakistani Patent Application No. 190/2003, issued Jul. 20, 2009.
Interview Summary for U.S. Appl. No. 10/933,674, dated Jan. 7, 2009.
Luo et al., "Chapters 2 and 3,", *Medicament Adjuvant Dictionary*: 16-22 (1995).
Luo et al., "Cyclodextria,", *Medicament Adjuvant Dictionary*: 504, 511 (1995).
Luomingsheng, Gaotianhui, *Medicament Adjuvant Dictionary*, publishing press of science and technology of SiChuang: 16-22, 504-511 (1995).
Martinez et al., "Applying the Biopharmaceutics Classification System to veterinary pharmaceutical products," (Part 1: Biopharmaceutics and Formulation Consideration) *Advanced Drug Delivery Reviews* 54:805-824 (2002).
Montoussé et al, "Extrusion-Spheronization Manufacture of Gelucire® Matrix Beads", *Drug Development and Industrial Pharmacy*, 25(1), 75-80 (1999).
Office Action for Canadian Patent Application No. 2,477,890, dated Mar. 10, 2010.
Office Action for Korean Patent Application No. 10-2004-7013775, dated Feb. 25, 2010.
Office Action for Polish Patent Application No. P 372579, dated Jan. 18, 2010.
Office Action for Polish Patent Application No. P 372579, dated Mar. 31, 2010.
Office Action for Polish Patent Application No. P 372579, dated Sep. 9, 2009.
Office Action for U.S. Appl. No. 10/933,674, dated Nov. 5, 2007.
Office Action for U.S. Appl. No. 11/276,577, dated Nov. 5, 2007.
Office Action for U.S. Appl. No. 10/933,674, dated Dec. 22, 2008.
Office Action for U.S. Appl. No. 11/276,577, dated Dec. 22, 2008.
Office Action for U.S. Appl. No. 11/276,577, dated Jun. 5, 2008.
Office Action for U.S. Appl. No. 10/933,674, dated Jun. 4, 2008.
Office Action for U.S. Appl. No. 10/933,674, dated Jul. 15, 2009.
Office Action for U.S. Appl. No. 11/276,577, dated Jul. 15, 2009.
Substantive Examination Report for Kingdom of Saudi Arabia, issued Mar. 10, 2007.
Translation of Substantive Examination Report for Pakistani Patent Application No. PK 190/2003, issued Mar. 15, 2008.
Voorspoels et al., "Pharmacokinetics of florfenicol after treatment of pigs with single oral or intramuscular doses or with medicated feed for three days." *The Veterinary Record* 145:397-9 (1999).
Notice on the Fifth Office Action for Chinese Patent Application No. 03805386.1, dated May 25, 2011. English translation provided.
Fawaz et al., "Bioavailability of Norfloxacin from PEG 6000 Solid Dispersion and Cyclodextrin Inclusion Complexes in Rabbits," *International Journal of Pharmaceutics* 132:271-275 (1996).
Official Communication issued in Brazilian Patent Application No. PI0308231-8, dated May 8, 2012 (5 pages).
Informal Translation of the Unfavourable Opinion for Official Communication issued in Brazilian Patent Application No. PI0308231-8, dated May 8, 2012 (3 pages).
Office Action (U.S. Appl. No. 12/815,781), dated Feb. 28, 2012 (15 pages).

* cited by examiner

IMMEDIATE RELEASE PHARMACEUTICAL GRANULE COMPOSITIONS AND A CONTINUOUS PROCESS FOR MAKING THEM

CROSS REFERENCE TO RELATED APPLICATIONS

This application is a continuation of U.S. patent application Ser. No. 11/276,577 filed Mar. 6, 2006, which is a continuation-in-part of U.S. patent application Ser. No. 10/933,674, filed Sep. 3, 2004, which is a continuation-in-part of International Application No. PCT/BE03/00040, filed Mar. 5, 2003, which was published in English under PCT Article 21(2), and which claims benefit of British Patent Application No. 0205253.8, filed Mar. 6, 2002, the disclosures of which are hereby incorporated by reference in their entirety.

FIELD OF THE INVENTION

The present invention is in the field of drug delivery systems and immediate release technology. Particularly, the invention is in the field of immediate or fast release pharmaceutical solid, preferably granule, compositions. More specifically, the invention relates to such compositions with low to moderate and even high drug loading for immediate or fast release of drugs which have low or very low solubility in water. The invention also relates to various solid pharmaceutical dosage forms such as sachets, gelules and tablets including such immediate or fast release pharmaceutical granule compositions. Still more specifically, the invention relates to immediate or fast release water-soluble granule veterinary compositions which can readily be administered to animals together with drinking water. Finally the invention relates to a continuous process for manufacturing said immediate or fast release pharmaceutical or veterinary granule compositions.

BACKGROUND OF THE INVENTION

Some general considerations relating to drug formulation are provided herein in order to understand the constraints applicable to the formulation of drugs which have low solubility in water and at the same time the kind of pharmaceutical solid formulations to which the present invention relates.

Tablets and capsules are generally unsuitable for administering high doses of biologically active ingredients since individual large dosage forms are difficult to swallow or necessitate the administration of several tablets or capsules at a time, leading to impaired patient compliance.

Hard gelatin capsules are known as a conventional pharmaceutical dosage form. Their sizes have been standard since the start of industrial manufacture of drug compositions, ranging from 5 (corresponding to a volume of 0.13 ml) up to 000 (corresponding to a volume of 1.36 ml). Thus, when a large amount of ingredient is required for each dosage unit, depending on the bulk density of the formulation, it may be necessary to use large size capsules which are too large to swallow or, even worse, a size 000 capsule may be too small to receive the said amount. Pellets and granules have been filled into hard gelatin capsules to be used as conventional or controlled release dosage forms, however the latter are rather difficult to manufacture.

The concept of tabletting coated active ingredient particles is therefore of major interest. Attempts have been made to produce tablets comprising microcapsules because of the advantages resulting from the microencapsulated substance being protected from external influences and vice-versa, e.g. increased stability, reduced chances of irritations or undesirable reactions with other components in a mixture, ability to mask unpleasant tastes and smells, etc. However, compaction of coated beads or pellets for making tablets encounters many difficulties and problems. As is well known in the pharmaceutical industry, beads or pellets are quite distinguishable from granules. Beads can be defined as small, free-flowing spherical or sphere-like particulates manufactured by pelletization, i.e. the agglomeration of fine powders or granules of drug substances and excipients using appropriate processing equipment. As opposed to the process of granulation, the production of beads by pelletization results in a larger average size and a narrower size-range distribution.

Another difficult problem is the formulation of drugs having low or very low water-solubility into solid dosage forms for immediate release. Few solutions to this problem have been disclosed in the art. For instance, U.S. Patent Publication No. 2001/0048946 provides solid dosage forms of sparingly water-soluble pharmaceutical agents, i.e. solid or crystalline drugs having a water-solubility of 10 to 33 μg/ml at 25° C., such as glitazones. More particularly, this document discloses a pharmaceutical composition in the form of a solid particulate dispersion of such a pharmaceutical agent dispersed throughout a matrix of a water-soluble polymer such as polyvinylpyrrolidone, hydroxypropyl cellulose, or hydroxypropyl methylcellulose. In a preferred embodiment, the particulate pharmaceutical agent is dispersed in the water-soluble polymer in a weight ratio of about 10% to about 90% active ingredient to about 90% to about 10% polymer. Other conventional excipients such as glycerin, propylene glycol, Tween, stearic acid salts and the like can be added.

U.S. Patent Publication No. 2001/0044409 discloses a process for the preparation of a poorly water soluble drug in solid dispersion comprising the steps of (a) blending the drug with a carrier, (b) dissolving a surfactant and a plasticizer/solubilizer in water, (c) spraying the surfactant-plasticizer/solubilizer solu-tion onto the drug/carrier mixture in a fluid bed granulator, (d) extruding the resulting granulation through a twin screw extruder with at least one heating zone, and (e) milling the extrudate to a powdery mass of the solid drug dispersion. Within the scope of this process, said carrier may be selected from the group consisting of polyvinylpyrrolidone, high molecular weight polyethylene glycol, urea, citric acid, vinyl acetate copolymer, acrylic polymers, succinic acid, sugars and mixtures thereof; the said plasticizer/solubilizer may be selected from the group consisting of low molecular weight polyethylene glycol, propylene glycol, glycerin, triacetin, triethyl citrate, sugar alcohols and mixtures thereof, and the said surfactant may be selected from the group consisting of Tween, Span, Pluronics, polyoxyethylene sorbitol esters, monodiglycerides, polyoxyethylene acid polyoxyethylene alcohol and mixtures thereof. This process suffers from the disadvantage of providing a heating zone in the twin screw extruder and consequently a need for controlling and monitoring the temperature profile of the extruder for efficient quality control.

However, none of the above processes appear to be successful in formulating solid dosage forms of drugs having very low water-solubility, i.e. a solubility lower than 10 μg/ml, preferably lower than 5 μg/ml. This problem is applicable to a large number of drugs, including those belonging to the family of diamino-pyrimidines, such as stated in U.S. Pat. No. 6,211,185.

U.S. Pat. No. 3,639,637 discloses oestrogen compositions for the preparation of stable aqueous suspensions that can be sprayed onto animal feed, comprising (by weight) 70-95% of water-dispersible gel-forming microcrystalline cellulose and 5-30% of finely-divided diethylstilbestrol (a compound which is virtually insoluble in water) and optionally further up to one third of the weight of the composition of a hydrocolloid selected from the group consisting of sodium carboxy-methylcellulose, methylcellulose and hydroxyethylcellulose. The two latter cellulose compounds are known, namely from EP-A-403,383, to contribute to an extended linear drug release rate.

EP-A-352,190 discloses a solid pharmaceutical unit with a delayed dissolution of the active ingredient, i.e. allowing retention of the active ingredient and avoiding its complete and immediate availability by a simple contact with an aqueous liquid medium. It further discloses in example 9 paracetamol micro-granules obtained from a mixture of 182 g paracetamol (a drug belonging to class I of the Biopharmaceutical Classification System and having a water-solubility of 14 mg/ml), 728 g microcrystalline cellulose (AVICEL PH 101) and 90 g sodium carboxymethylcellulose. EP-A-352,190 however does not teach using a cyclodextrin compound as a drug dissolution enhancer.

U.S. Pat. No. 5,362,860 discloses (see table VI, example C) a composition with improved storage stability comprising (by weight) 0.05% of a pyridine based oxime (a drug undergoing hydrolysis into an aldehyde in an acidic environment), 70% cyclodextrin, 3% crosscarmellose (a crosslinked polymer) and 20.95% microcrystalline cellulose.

WO-A-99/12,524 solves the problem of drug formulations with both a relatively fast or quick onset of the therapeutic effect and the maintenance of a therapeutically active plasma concentration for a relatively long period of time, by providing an oral modified release multiple-units composition wherein the unit dosage form comprises at least (i) a first fraction being able to release at least 50% of the drug within the first 20 minutes of a certain dissolution method, and (ii) a second fraction for delayed and extended release of the drug. The multiple-units of the first fraction may be granulates or, provided that a surfactant is added to the formulation, coated or uncoated pellets. Formulation of the first fraction depends on the specific drug but typically includes wet-granulation, and an antacid-like or other alkaline substance was found to have a pronounced increasing effect on the release rate.

U.S. Pat. No. 5,646,131 discloses (example 4) rapidly dissolving capsules containing a granulate formulation of a water-insoluble or sparingly soluble drug, such as terfenadine (less than 0.01 mg/ml water-solubility), surfactants (Tween 80 and sodium lauryl sulfate), cyclodextrin, Avicel PH 101 (microcrystalline cellulose) and a disintegrant/swelling agent (Primojel®, i.e. sodium carboxy-methyl starch) in a weight ratio of 10:72 to Avicel. These capsules provide better drug absorption, due to the presence of cyclodextrin, as evidenced by the figure showing a 90% drug release within 45 minutes.

Elbers et al. in *Drug Development and Industrial Pharmacy* (1992) 18(5):501-517 discloses theophylline pellets with a drug loading from 10 to 50% obtained by extrusion-spheronization with Avicel® RC 581 (a blend of microcrystalline cellulose and sodium carboxymethylcellulose). Theophylline is a drug with a water-solubility of 8 mg/ml (according to Merck Index, 12$^{th}$ edition 1996) and high permeability (according to FDA Guidance to Industry, 2000), thus belonging to class I of the Biopharmaceutical Classification System.

U.S. Pat. No. 4,235,892 discloses a series of 1-aryl-2-acylamido-3-fluoro-1-propanol antibacterial agents including D-(threo)-1-p-methylsulfonyl phenyl-2-dichloroacetamido-3-fluoro-1-propanol, an antibacterial agent known as florfenicol and useful for veterinary purposes. Florfenicol has low solubility in water (about 1.3 mg/ml), as well as in many pharmaceutically acceptable organic solvents such as 1,2-propanediol, glycerin, and benzyl alcohol. For oral administration, these 1-aryl-2-acylamido-3-fluoro-1-propanol may be compounded in the form of tablets, or may even be admixed with animal feed. U.S. Pat. No. 4,235,892 therefore discloses making tablets by compressing granules of a composition comprising the said 1-aryl-2-acylamido-3-fluoro-1-propanol (in a drug loading range from 8.3% to 41.7% by weight), lactose, microcrystalline cellulose, starch and magnesium stearate.

The Biopharmaceutical Classification System (hereinafter referred as BCS) according to G. Amidon et al. in *Pharm. Res.* (1995) 12:413-420 provides for two classes of poorly soluble drugs, i.e. Class II and Class IV, and a class of highly soluble drugs, i.e. Class I. According to M. Martinez et al., Applying the Biopharmaceutical Classification System to Veterinary Pharmaceutical Products (Part I: Biopharmaceutics and Formulation Consideration) in *Advanced Drug Delivery Reviews* (2002) 54:805-824, a drug substance should be classified as highly soluble when the highest dose strength is soluble in at most 250 ml of aqueous media over the pH range 1-7.5. In view of its water solubility (1.3 mg/ml) and of a maximal dose of 20 mg/kg for pigs, it is easy to calculate that the highest dose strength of florfenicol administered to pigs is soluble in an amount of water which is well above the limit value for the definition of a class I BCS highly soluble drug. Furthermore it is known from J. Voorspoels et al. in *The Veterinary Record* (October 1999) that florfenicol has a good oral bioavailability, so that it can be classified as a Class II compound as it is not a highly soluble drug and it shows no absorption problems.

U.S. Pat. No. 6,368,634 discloses a solid preparation suitable for a substantially immediate release of an active agent having a low or very low solubility, for example wherein more than 80% of the active agent is released within 2 hours, preferably within 1 hour or less from the administration. This solid preparation is obtained by pelletisation, i.e. an agglomeration process whereby fine powders or granules are shaped into fine, free-flowing units (pellets) with a particle size above 250 μm. The pellets of this solid preparation comprise one or more carriers (which may be polymers, or inorganic carriers such as talc, montmorillonite, bentonite, clay or calcium phosphate) and an active ingredient dissolved in a liquid phase (liquid as such or to be liquified for example by means of shear or temperature) which may be an oil or fat, a tensio-active agent or a polar co-solvent (such as polyethylene glycol, glycerol or propylene glycol). In U.S. Pat. No. 6,368,634 the active ingredient is dissolved in a liquid solubilizer (the weight ratio solubilizer/active agent being greater than 4) which is fixed on solid carrier particles preferably with a particle size below 500 μm such as microcrystalline cellulose, the resulting mixture being then transformed into pellets using a suitable batch technique such as extrusion/spheronisation, fluid-bed technology, rotary granulation. As a result the active ingredient is already in solution inside the dosage form (i.e. pellets) and hence is very quickly released from the dosage form upon contact with aqueous media. Therefore according to U.S. Pat. No. 6,368,634 it is essential to have a liquid phase in which the active ingredient can dissolve to obtain the reported dissolution profiles.

FIGS. 6 and 7 of U.S. Pat. No. 6,368,634 clearly illustrate that the active ingredient is no longer in its crystalline form inside the dosage form, but has gone into solution in the solubilizer. No peaks of crystalline hydrochlorothiazide (at 2θ=19°) are present in the X-ray diffraction pattern of pellets containing 3.5% by weight hydrochlorothiazide (HCT) and 32% by weight polyethylene glycol with a molecular weight of 400, as shown in FIGS. 6B and 6C. The importance of the active agent being dissolved in the liquid solubilizer is clearly shown in example 4 in combination with FIGS. 5 and 7 of U.S. Pat. No. 6,368,634. FIG. 5 shows a higher dissolution rate after 6 months storage of pellets containing 3.5% by weight HCT and 21% by weight polyethylene glycol hydrogenated castor oil. Immediately after preparation a crystalline peak of HCT was still visible (FIG. 7A), whereas it had disappeared after 6 months storage (FIG. 7B), i.e. all HCT crystals had dissolved, this behaviour being also indicative of a need for controlling drug formulation stability during storage. An increased dissolution rate was obtained after heat treatment of the pellets immediately after preparation, this again corresponding to the complete drug fraction going into solution as shown in FIG. 7C.

A limitation of the technology disclosed in U.S. Pat. No. 6,368,634 is that it only allows to increase the dissolution rate of formulations containing a low content of active ingredient (i.e. drug loading) since the amount of liquid phase (solubilizer) that can be fixed onto the solid carrier particles is limited to a weight ratio solubilizer/particles from 1:5 to 1:2, and the active ingredient further needs to dissolve into the solubilizer. This limitation is well illustrated in U.S. Pat. No. 6,368,634 teaching drug loadings in a range from about 1% by weight (examples 1 and 9) to about 6.7% by weight (example 5). This limitation was confirmed by our experiments performed while preparing a pellet formulation based on the teachings of U.S. Pat. No. 6,368,634 but containing 20% by weight of a veterinary active ingredient. The release rate of this ingredient from the pellets was low and this slow drug release from the pellets was also reflected in low plasma levels of broiler chickens after administration of this formulation via drinking water.

Furthermore, U.S. Pat. No. 6,368,634 describes the dosage form as pellets which are produced by a suitable batch technique such as fluid-bed technology, rotary granulation or, preferably, extrusion-spheronisation. The extrusion-spheronisation process is a multi-step process capable of making uniformly sized preferably spherical particles (pellets). The following steps are required: (a) dry mixing, (b) wet granulation (i.e. formation of a wet mass, e.g. in U.S. Pat. No. 6,368,634 through the addition of a liquid phase and water (in order to get sufficient plasticity for extrusion), (c) extrusion (i.e. forming the wet mass into long rod-shaped particles), (d) spheronisation (breaking the rod-shaped particles into smaller pieces and rounding the individual particles into spheres) and (e) drying (removal of water added during granulation). Another limitation of the technology disclosed in U.S. Pat. No. 6,368,634 is thus that the stickiness of the wet mass formed in step (b) should not exceed a level where its extrusion in step (c) would become impossible and/or would block the extruder. This proviso implies significant limitations on the liquid solubilizer that may be used according to U.S. Pat. No. 6,368,634. In particular, the latter document does not teach or suggest the use of maltodextrins, and the skilled person knows that a mixture of water and a maltodextrin would have a stickiness much higher than permitted for extrusion. Another limitation of this technology is the need for an energy-consuming drying step in the final stage of the extrusion-spheronisation process.

Therefore, there is still a need in the art for formulating poorly soluble drugs classifiable as or belonging to Class II or Class IV of the Biopharma-ceutical Classification System not only into formulations with low drug contents (such as known from U.S. Pat. No. 6,368,634) but also into formulations with moderate and even high drug contents. There is also a need in the art for making formulations of poorly soluble drugs classifiable as or belonging to Class II or Class IV of the Biopharma-ceutical Classification System by means of a continuous production method, not a batch-wise production method, in order to decrease their production cost. There is also a need in the art for making formulations of poorly soluble drugs classifiable as or belonging to Class II or Class IV of the Biopharma-ceutical Classification System by an energy-saving production method which does not require a drying step, in order to decrease their production cost. There is also a need in the art for formulating poorly soluble drugs classifiable as or belonging to Class II or Class IV of the Biopharma-ceutical Classification System as granules, not pellets. There is also a need in the art for formulating poorly soluble drugs classifiable as or belonging to Class II or Class IV of the Biopharmaceutical Classification System in the absence of a costly pharmaceutical grade material such as microcrystalline cellulose.

There is a specific need in the art to provide a solid formulation of drugs with a water-solubility like florfenicol or lower. Florfenicol is a drug for administration to warm-blooded animals, such as cattle with naturally-occurring bovine respiratory disease, swine, sheep, goats and poultry, which at present is mainly available in the form of injectable solutions. Until now the skilled person has failed in the design of such a solid formulation of florfenicol, which can further be admixed with animal feed if necessary. There is therefore a need in the art for a florfenicol formulation in the form of a water-soluble granulate for administration to animals together with drinking water. Also there is a need for a solid formulation for many low solubility drugs for human and veterinary therapies.

SUMMARY OF THE INVENTION

The present invention is based on the unexpected finding that drugs classifiable as or belonging to Class II (poorly soluble, highly permeable) or Class IV (poorly soluble, poorly permeable) of the Biopharmaceutical Classification System, including drugs having very low water-solubility, can be successfully formulated into immediate or fast release pharmaceutical solid dosage forms provided that:

(1) they are admixed in suitable proportions with a first pharmaceutically acceptable excipient comprising a dextrin-containing compound or, in a less preferred embodiment, a blend of microcrystalline cellulose and a swellable polymer, or a mixture of the said dextrin-containing compound and the said blend, and with a second pharmaceutically acceptable excipient being a non-aqueous wetting compound comprising at least a solid fraction, and that (2) they are formulated into granule compositions, not pellet compositions.

Preferably, these granule formulations are advantageously obtained by a continuous manufacturing process involving a low temperature extruding step in an extruding means. Based on the above teachings, the invention also provides various pharmaceutical dosage forms such as sachets and solid shaped articles such as tablets and hard gelatin capsules including the said granule compositions. The invention also provides water-soluble granule compositions of poorly soluble drugs that may be administered to animals in admixture with drinking water. The invention also relates to the treatment of bacterial infections in human beings and in animals, such as poultry, pigs, cattle (e.g. the treatment of bovine respiratory disease) and fish, by the oral administration to the human being or animal of an effective amount of the above-referred immediate or fast release pharmaceutical granule compositions.

DEFINITIONS

Figure 1:
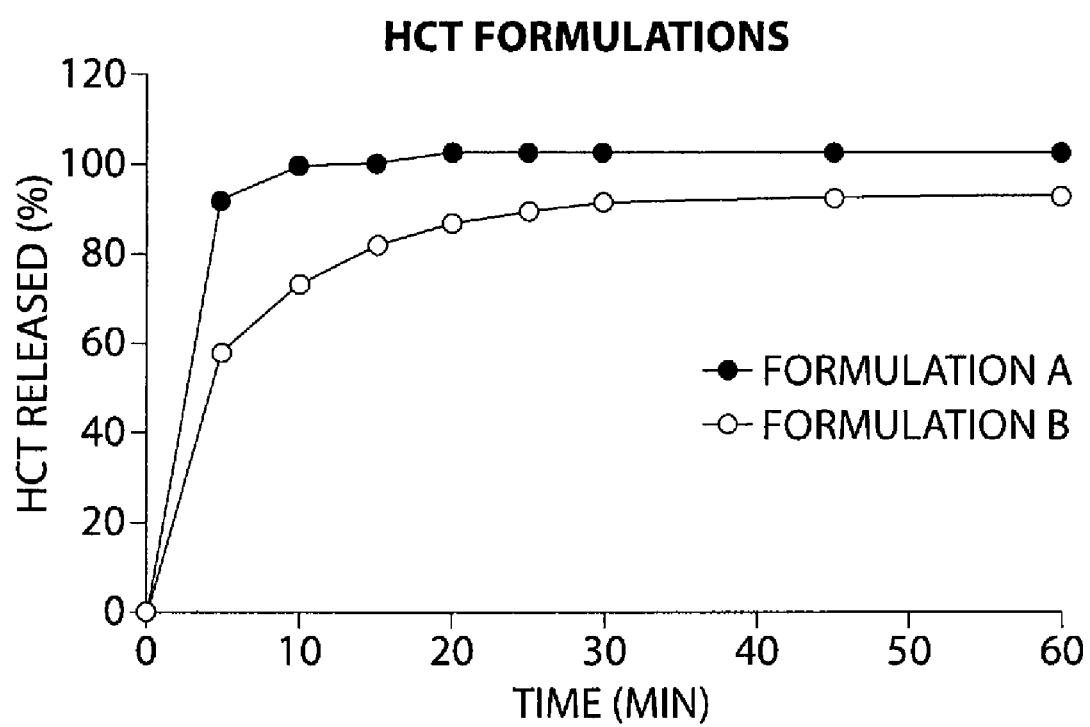
FIG. 1 represents the release, as a function of time, of hydrochloro-thiazide from a granule composition according to one embodiment of the invention.

The terms "low drug content" and "low drug loading" as used herein, unless otherwise stated, are intended to mean a drug content, with respect to the total solid formulation, in a range below about 7% by weight, preferably at least about 0.5% by weight.

The terms "moderate drug content" and "moderate drug loading" as used herein, unless otherwise stated, are intended to mean a drug content, with respect to the total solid formulation, in a range from about 7° A, by weight to about 20% by weight.

The terms "high drug content" and "high drug loading" as used herein, unless otherwise stated, are intended to mean a drug content, with respect to the total solid formulation, in a range above about 20% by weight.

The term "solid shaped article" as used herein means any article being in a hard solid state at temperatures not exceeding about 60° C. and having a definite geometrical shape, such as for instance ordinary tablets, effervescent tablets, pills, lozenges and other compressed dosage forms.

The term "immediate release" as used herein means a release of at least about 50% of a drug within 30 minutes in water, preferably a release of at least about 70% of said drug within 10 minutes in water, and more preferably a release of at least about 80% of said drug within 10 minutes in water, under physiological temperature and pH conditions. The term "fast release" as used herein means a release from about 40% to about 50% of a drug within 30 minutes in water, under physiological temperature and pH conditions.

DETAILED DESCRIPTION OF THE INVENTION

In a first embodiment, this invention relates to an immediate or fast release pharmaceutical solid composition comprising at least one drug (i) classifiable as Class II (poorly soluble, highly permeable) or Class IV (poorly soluble, poorly permeable) of the Biopharmaceutical Classification System, e.g. a drug having very low water-solubility such as defined herein, wherein said drug is present in said solid composition in a low drug content, a moderate drug content or a high drug content, i.e. said drug constitutes at least about 0.5% by weight but no more than 50% by weight, for instance from 0.5% to about 20% by weight (low and moderate drug loadings), preferably from 1 to 15% by weight, or alternatively from 20% to 50% by weight (high drug loadings) of the solid composition, wherein said solid composition is in the form of granules comprising one or more pharmaceutically acceptable excipients, wherein said one or more pharmaceutically acceptable excipients comprise (ii) a first excipient selected from the group consisting of:
  blends of a microcrystalline cellulose and a swellable polymer in respective amounts such that the weight ratio of the said polymer to the microcrystalline cellulose in the blend is above about 2:100 and up to about 30:100,
  one or more dextrin-containing compounds selected from the group consisting of maltodextrins, cyclodextrins and derivatives thereof, and
  mixtures of the said dextrin-containing compounds and the said blends, and (iii) a wetting amount of a second excipient being a non-aqueous wetting compound or meltable compound and comprising a solid fraction and optionally a liquid fraction.

In a second embodiment, this invention relates to a continuous process for manufacturing the aforesaid immediate or fast release solid pharmaceutical composition. More particularly, this invention provides a continuous process for manufacturing a pharmaceutical granule composition comprising at least one drug (i) classifiable as Class II or Class IV of the Biopharma-ceutical Classification System in an amount of no more than about 50% by weight, for instance from 0.5% to about 20% by weight (low and moderate drug loadings), preferably from 1 to 15% by weight, or alternatively from 20% to 50% by weight (high drug loadings), of said pharmaceutical composition, a first excipient (ii) being a dextrin-containing compound in an amount from 40 to 85% by weight of said composition, and a second excipient (iii) comprising a solid fraction and optionally a liquid fraction, said second excipient (iii) being in an amount from 15 to 40% by weight of the composition and being selected from the group consisting of polyethylene glycols and polypropylene glycols having weight number molecular weights between about 300 and 10,000 (preferably between 300 and 5,000), glycerol, propylene glycol and glycerides, comprising the steps of:

(a) homogenising a mixture comprising the drug (i) classifiable as Class II or Class IV of the Biopharmaceutical Classification System, e.g. a drug having low or very low water-solubility, the first excipient (ii) and the solid fraction of the second excipient (iii), (b) feeding the mixture obtained in step (a) and optionally the liquid fraction of the second excipient (iii) into an extruding means having one or more mixing zones and one or more transport zones, and (c) extruding the materials fed in step (b) while operating the extruding means at a temperature not above the melting temperature of the solid fraction of the second excipient until an immediate release pharmaceutical granule composition is obtained.

More detailed ways of implementing the invention will now be described in more details by referring both to the immediate or fast release pharmaceutical granule composition and the process for manufacturing the same. In a first but less preferred embodiment of the invention, the first excipient (ii) may be a blend of a microcrystalline cellulose and a swellable polymer and the said swellable polymer may be an uncrosslinked carboxyalkylcellulose metal salt such as for instance sodium or calcium carboxymethylcellulose.

In a preferred embodiment of the invention the first excipient (ii), whatever its nature (i.e. the aforesaid blend or a dextrin-containing compound such as a maltodextrin), may be present in the pharmaceutical granule composition in an amount from about 40% to about 85% by weight of the said composition.

Microcrystalline cellulose, in particular a pharmaceutical grade thereof, is well known in the art of pharmaceutical industry for its high surface porosity and its outstanding capillary character. It is available from a variety of commercial sources, e.g. Avicel® PH 101 (commercially available from FMC Corporation, Philadelphia, Pa.), Emcocel® (Mendell), Vivocel® (JRS) and the like. Microcrystalline cellulose is a partially purified depolymerized form of cellulose and is obtained by treating pulps derived from fibrous plant material with mineral acid. The acid preferentially attacks the less ordered or amorphous regions of the cellulose polymer chain, thereby exposing and freeing the crystalline sites which form cellulose crystallite aggregates. The reaction mixture is washed to remove the degraded byproducts, the resulting wet-cake is freed of water and the dried cellulose crystallite aggregates, or more commonly microcrystalline cellulose, recovered. Microcrystalline cellulose is a white, odourless, tasteless, relatively free-flowing powder, insoluble in water, organic solvents, dilute alkalies and dilute acids.

A swellable polymer suitable for use in the blend being an embodiment of the first excipient (ii) of the present invention may be defined herein preferably as an ionic hydrocolloid polymer which is easily miscible with microcrystalline cellulose and which, on its own, is able to form a colloidal suspension in an aqueous environment, the colloidal particles e.g. forming a three-dimensional network or grid-like structure throughout the liquid phase. Suitable examples of such polymer include pharmaceutical grades of sodium carboxymethylcellulose such as commercially available under the tradenames Nymcel®, Tilose® and Blanose® (Aqualon). Preferably, the swellable polymer is a low molecular weight and/or low viscosity polymer. For instance when the swellable polymer is an uncrosslinked carboxyalkylcellulose metal salt, it should preferably have sufficient unsubstituted hydroxyl groups in order to hydrogen bond to the microcrystals of the microcrystalline cellulose upon drying and the substituent groups should have ability to impart water-solubility. The degree of substitution of the carboxyalkyl-cellulose should preferably not exceed about 0.9 and more preferably be within a range of 0.5 to 0.9. Also, the viscosity of a 2% aqueous solution of the swellable polymer at 20° C. should preferably be below 1,000 mPa·s, more preferably within a range from about 20 to 800 mPa·s.

The swellable polymer and the microcrystalline cellulose being part of the first excipient (ii) may be afforded separately at the time of making the pharmaceutical granule compositions of the present invention or they may be present in the form of a co-processed blend.

A co-processed blend of the swellable polymer together with microcrystalline cellulose is readily available, e.g. as Avicel® RC 581 and Avicel CL 611 (both commercially available from FMC Corporation), both well known in the art in the form of pharmaceutically acceptable grades. This cellulosic blend may alternatively be prepared by bringing the two blend components into intimate contact under suitable conditions, for instance by subjecting the washed filter cake containing microcrystalline solids from the acid degradation of cellulose to intense attritive forces, thus resulting in a further break up of the cellulose crystallite aggregates and an increase in sub-micron particles. As the attrition proceeds, a sufficient amount of the swellable polymer (e.g. sodium carboxymethyl cellulose) is added to the aqueous mixture in order to at least partially coat the individual microcrystals of the microcrystalline cellulose. Upon completion of the attrition, the blend is dried and recovered. The dried product is readily redispersible in aqueous media to give gels. Important for its effectiveness in the present invention is the fact that this blend is a non-disintegrating water-insoluble water-dispersible powder before it is granulated in admixture with the poorly soluble drug and the second excipient. Preferably at least about 1% by weight and more preferably at least about 30% by weight of the powder blend particles have an average size not greater than about 1.0 µm as determined by electron microscopic examination.

For optimal efficiency, the weight ratio of the said swellable polymer to the microcrystalline cellulose in this first but less preferred embodiment of the first excipient (ii) for the immediate or fast release pharmaceutical granule composition of the invention, or respectively in the (co-processed) blend as above defined, should be above about 2:100 and up to about 30:100, preferably between about 7:100 and 20:100.

In a much preferred second embodiment of the invention, the first excipient (ii) is a dextrin-containing compound such as described hereinafter.

Drug dissolution enhancing agents, in particular being dextrin-containing compounds such as maltodextrins, cyclodextrins and related substances such as chemically-modified derivatives thereof, in particular their pharmaceutically acceptable grades, are well known in the art and are available from a variety of commercial sources. They may be collectively referred as starch cyclic linear degradation products containing 6 to 8 glucose residues, or alternatively as cyclic oligosaccharides composed of L-glucose molecules linked by α or β osidic bonds having a toric form. Among the above group of compounds, special attention will be paid to cyclodextrins, and still more preferably, to maltodextrins for inclusion in the first excipient (ii) of the pharmaceutical granule composition. Cyclodextrins are crystalline (usually white powder), non-hygroscopic, cyclic oligosaccharides derived from starch. Among the most commonly useful are α-, β-, and γ-cyclodextrins which have respectively 6, 7, and 8 glucose units. Suitable representative embodiments of cyclodextrin derivative enhancing agents include 2-hydroxypropyl-β-cyclodextrin, dimethyl-β-cyclodextrin, 2-hydroxyethyl-β-cyclodextrin, 3-hydroxypropyl-β-cyclodextrin, and trimethyl-β-cyclodextrin. Maltodextrins occur as non-sweet, odourless, white powders or granules and are saccharide mixtures of polymers that consist of D-glucose units with a dextrose equivalent less than 20.

Preferably the amount of the first excipient (ii), particularly in the form of a dextrin-containing compound, represents from about 40% by weight to about 85% by weight, more preferably from 50% to 75% by weight of the immediate or fast release pharmaceutical granule composition of the invention, depending on the amounts of the other excipients (such as fillers) that may optionally be present therein.

According to the invention, the aforesaid immediate release is a release of at least about 50% of the said drug within 30 minutes in water, preferably a release of at least about 70% of the said drug within 10 minutes in water, and more preferably a release of at least about 80% of the said drug within 10 minutes in water, preferably under physiological temperature and pH conditions. As shown in the following examples, the present invention is also successfully applicable to drugs having low, but not very low, water-solubility but which are relatively highly dosed drugs (i.e. constitute from about 10% to about 20% by weight of the composition) for therapeutic efficiency, such as florfenicol.

The immediate or fast release pharmaceutical granule compositions of this invention may further comprise one or more pharmaceutically acceptable fillers. The aforesaid pharmaceutically acceptable fillers may be selected for instance from hydrocolloids (such as, but not limited to, xanthan gum), binding agents, glidants, lubricants, surfactants and diluents. The term "pharmaceutically acceptable filler" as used herein is intended to refer to any material which is inert in the sense that it does not have any therapeutic and/or prophylactic effect per se but does not adversely interfere with the therapeutic or prophylactic property of the drug or pharmaceutical active ingredient being formulated. The nature and amount of such fillers are not critical to the present invention. They include for instance binding agents such as, but not limited to, starch, gelatin, glucose, alginic acid, sodium and calcium alginates, water-soluble acrylic (co)polymers, polyvinylpyrrolidone, polyamino-acids, ethylene-vinyl acetate copolymers and the like; natural and synthetic mineral fillers or glidants such as, but not limited to, fumed (colloidal) silica (e.g. commercially available under the tradename Aerosil®), magnesium silicates such as talc, diatomaceous earth, aluminium silicate such as kaolinite, montmorillonite or mica, magnesium aluminium silicate such as attapulgite and vermiculite, carbon such as charcoal, sulphur and highly dispersed silicic acid polymers; water-soluble diluents such as, but not limited to, lactose, sorbitol and the like.

Surfactants are another class of pharmaceutically acceptable fillers which may be useful for including into the immediate or fast release pharmaceutical granule compositions of this invention. Suitable surfactants for this purpose preferably have HLB values ranging from about 1 to about 20. Non-limiting examples thereof are as follows:
(a) reaction products of natural or hydrogenated vegetable oils, and ethylene glycol, i.e. polyoxyethylene glycolated natural or hydrogenated vegetable oils, e.g. polyoxyethylene glycolated natural or hydrogenated castor oils commercially available under the trade names Cremophor® RH-40, Cremophor® RH-60, Cremophor® EL, Nikkol® HCO-40, Nikkol® HCO-60 and Arlatone® 289;
(b) polyoxyethylene sorbitan fatty acid esters, e.g. mono-, di- and tri-lauryl, palmityl, stearyl or oleyl esters such as products commercially available under the trade name Tween® including polyoxyethylene sorbitan mono-laurate, polyoxyethylene sorbitan mono-palmitate (Tween® 40) and polyoxyethylene sorbitan mono-oleate (Tween® 80);
(c) polyoxyethylene fatty acid esters, e.g. polyoxyethylene stearic acid esters, commercially available under the trade names Mirj® and Cetiol® HE;
(d) non-ionic polyoxyethylene-polyoxypropylene copolymers, e.g. commercially available under the trade names Pluronic® and Emkalyx®;
(e) non-ionic polyoxyethylene-polyoxypropylene-polyoxyethylene block copolymers, e.g. commercially available under the trade names Lutrol® F68 (also known as poloxamer 188) and Lutrol® F127 (also known as poloxamer 407);
(f) dioctylsuccinate, dioctylsodiumsulfosuccinate, di-(2-ethylhexyl)-succi-nate, sodium lauryl sulfate or sodium N-methyl N-cocoyl taurate (commercially available as Adinol® CT95); and
(g) phospholipids, in particular lecithins, especially soybean lecithin.

Although the nature of pharmaceutically acceptable fillers being present in the immediate or fast release pharmaceutical granule compositions of this invention is not critical, it is however preferred when the first excipient (ii) is a dextrin-containing compound such as a maltodextrin, that the immediate or fast release pharmaceutical granule composition of the invention be substantially free of micro-crystalline cellulose. A particularly useful embodiment of this invention is when the first excipient (ii) is a dextrin-containing compound such as a maltodextrin, and the immediate or fast release pharmaceutical granule composition additionally comprises from about 1% by weight to about 6% by weight of one or more surfactants such as described hereinabove.

According to this invention, the drug (i) is classifiable as Class II or Class IV of the BCS and preferably has a water-solubility below about 2.5 mg/ml, even between 0.1 and 1 mg/ml (i.e. "very slightly soluble" as defined according to the United States Pharmacopeia), even below 0.1 mg/ml (i.e. "practically insoluble" as defined according to the United States Pharmacopeia), even below about 5 µg/ml and may even have a water-solubility as low as about 0.2 µg/ml, at room temperature and physiological pH. Non-limiting examples of such drugs include for instance flunixin, meglumine, febantel, chlorothiazide, hydrochlorothiazide, nimodipine, flufenamic acid, furosemide, mefenamic acid, bendroflumethiazide, benzthiazide, ethacrinic acid, nitrendipine, itraconazole, saperconazole, troglitazone, prazosin, atovaquone, danazol, glibenclamide, griseofulvin, ketoconazole, carbamazepine, sulfadiazine, florfenicol, acetohexamide, ajamaline, benzbromarone, benzyl benzoate, beta-methasone, chloramphenicol, chlorpropamide, chlorthalidone, clofibrate, diazepam, dicumarol, digitoxin, ethotoin, glutethimide, hydrocortisone, hydro-flumethiazide, hydroquinine, indomethacin, ibuprofen, ketoprofen, naproxen, khellin, nitrazepam, nitrofurantoin, novalgin, oxazepam, papaverine, phenylbutazone, phenyloin, prednisolone, prednisone, reserpine, spironolactone, sulfabenzamide, sulfadimethoxine, sulfamerazine, sulfamethazine, sulfamethoxy-pyridazine, succinylsulfathiazole, sulfamethizole, sulfamethoxazole (also in admixture with trimethoprim), sulfaphenazole, sulfathiazole, sulfisoxazole, sulpiride, testosterone and diaminopyrimidines. Suitable examples of diamino-pyrimidines include, without limitation, 2,4-diamino-5-(3,4,5-trimethoxy-benzyl) pyrimidine (known as trimethoprim), 2,4-diamino-5-(3,4-dimethoxybenzyl)pyrimidine (known as diaveridine), 2,4 diamino-5-(3,4,6-trimethoxybenzyl)pyrmidine, 2,4-diamino-5-(2-methyl-4,5-dimethoxybenzyl)pyrimidine (known as ormetoprim), 2,4-diamino-5-(3,4-dimethoxy-5-bromobenzyl)pyrimidine, and 2,4-diamino-5-(4-chloro-phenyl)-6-ethylpyrimidine (known as pyrimethamine). The above-mentioned drugs are known as belonging to Class II (poorly soluble, highly permeable) or Class IV (poorly soluble, poorly permeable) of the Biopharmaceutical Classification System according to G. Amidon et al. in *Pharm. Res.* (1995) 12:413-420. As will be appreciated by those skilled in the art, these drugs belong to various therapeutic classes, including diuretics, anti-hypertensive agents, anti-viral agents (particularly anti-HIV), antibacterial agents, antifungals, etc, and are not limited to human or veterinary use alone.

According to this invention, the granules of the immediate or fast release pharmaceutical granule composition preferably have a diameter ranging from about 100 and 2,500 µm.

The second excipient (iii) of the immediate or fast release pharmaceutical granule composition of this invention is preferably one which will not give rise to difficulties during extrusion and may suitably be selected from the group consisting of polyethyleneglycols and polypropyleneglycols having weight number molecular weights between about 300 and about 10,000, preferably between 300 and 5,000; glycerol; propylene glycol and glycerides (such as mono-, di- and triglycerides of polyethyleneglycol fatty acid esters, including those commercially available under the tradename Gelucire®). Suitable examples of the latter include those having both a portion derived from a glyceride and a portion derived from a polyethylene glycol ester. For instance, it is suitable to use polyglycosylated glycerides. The term "polyglycosylated glycerides" as used herein refers to a mixture of mono-, di- and triglycerides with polyethyleneglycol (PEG) mono- and diesters of $C_8$-$C_{18}$ fatty acids with a molecular weight preferably between about 200 and about 600, optionally further including glycerol and/or free PEG, the hydrophilic-lipophilic balance (HLB) value of which is controlled by the chain length of the PEG and the melting point of which is controlled by the chain length of the fatty acids, of the PEG and of the degrees of saturation of the fatty chains, and thus of the starting oil. Similarly the expression "$C_8$-$C_{18}$ fatty acids" as used herein denotes mixtures in various proportions of caprylic acid, capric acid, lauric acid, myristic acid, palmitic acid and stearic acid, when these acids are saturated, and the corresponding unsaturated acids. As is well known to the skilled person, the proportions of these fatty acids may vary as a function of the starting oils. Examples of the latter include, but are not limited to, saturated polyglycolized $C_8$-$C_{10}$ glycerides, such as the PEG-8 caprylate/caprate glyceride esters sold by Gattefosse Corporation under the tradename Labrasol; PEG-6 caprylic/capric glycerides sold by Huls Aktiengesellschaft under the trade name Softigen 767; PEG-60 corn glycerides sold by Croda under the trade name Crovol M-70; Ceteareth-20 sold by Henkel Corporation under the trade name Emulgin B2; diethyleneglycol monoethylethers sold by Gattefosse Corporation under the trade name Transcutol; a mixture of $C_8$-$C_{18}$ saturated polyglycosylated glycerides having a melting point within a range of about 42-48° C. and a HLB within a range of about 8 to 16 such as sold by Gattefosse Corporation under the trade names Gelucire 48/09, Gelucire 44/14 and Gelucire 42/12; and mixtures thereof in various proportions. When a polyethyleneglycol is used for instance, it may comprise a higher molecular weight solid fraction and a lower molecular weight liquid fraction, the latter acting as a plasticizer.

In a preferred embodiment of the invention the second excipient (iii), particularly when the first excipient (ii) is a dextrin-containing compound, may be present in the immediate or fast release granule composition of this invention in an amount from about 10% to about 40% by weight, more preferably from 15% to 40% by weight, most preferably from 20% to 30% by weight, of the said composition. In yet another preferred embodiment of the invention, the weight ratio between the liquid fraction and the solid fraction of the second excipient (iii) may be from 0:1 (no liquid fraction) to about 1:1, more preferably from 0:1 to about 1:2, most preferably not more than 1:3. In yet another more preferred embodiment of the invention, for instance when a maltodextrin is used as the first excipient (ii) and a polyethyleneglycol is used as the second excipient (iii), the weight ratio of the first excipient (ii) to the second excipient (iii) is in a range from about 1:1 to about 5:1.

According to this invention, the immediate or fast release pharmaceutical granule composition may optionally further comprise one or more other drugs different from the drug having poor water-solubility, but preferably belonging to the same therapeutic class, in particular when combined drug therapy is desired.

The continuous process for manufacturing a pharmaceutical granule composition of the present invention is preferably performed in an apparatus, such as a twin screw extruder, comprising a barrel having a granulation chamber provided with inlets for supplying the drug (i), the first excipient (ii) and the solid fraction of the second excipient (iii), and at least one continuously operated rotating transporting means. The said extruder is preferably operated at a temperature not above about 60° C., more preferably not above 45° C., most preferably at a temperature not above about 35° C., i.e. there is no need to provide a heating zone on the said extruder, therefore no need to provide sophisticated means for controlling and monitoring the temperature of the extruder. The extruder is preferably operated at a rotating speed between about 5 and 450 rpm, for instance between 5 and 300 rpm, depending upon whether low shear, medium shear or high shear is desired. The continuously operated rotating transporting means of the extruder comprises one or more mixing zones and one or more transport zones. The configuration and number of these zones may be widely varied, however at least one mixing zone is most preferred, being very advantageous to induce interaction between the various components of the composition to be extruded. The remaining of the screw may then consist of transportation zones. Single or twin lead discharge screws can be used. As is standard in this art, the length to diameter ratio of each rotating transporting means may be within a range from about 15 to about 60.

The present invention also provides solid shaped articles comprising a core consisting of an immediate or fast release pharmaceutical granule composition as defined hereinabove. This solid shaped article may be in the form of a tablet or a hard gelatine capsule. Methods for producing tablets, such as compression, or hard gelatine capsules from pharmaceutical granule compositions are well known to those skilled in the art. In the case of a tablet, the solid shaped article may further comprise a coating, according to standard practice in the art.

The solid shaped articles of the present invention may further optionally contain additives typically used in the formulation of such articles, for instance flavoring agents (such as anethole, benzaldehyde, vanillin, ethyl vanillin, ethyl acetate, methyl salicylate and the like), lubricants (such as magnesium stearate), sweeteners (such as sucrose, mannitol, aspartame, saccharin and its salts), colorants and/or buffering agents.

The present invention further provides a sachet comprising an immediate or fast release pharmaceutical granule composition as above defined.

The present invention provides a number of advantages over the existing formulations of poorly soluble drugs and over the existing methods of making the latter, such as:
  the same technology is able to formulate such drugs at low, but also at moderate and even high drug contents, as defined herein,
  the production cost of such formulations can be decreased by making use of a continuous, rather than batch-wise, process, and/or by avoiding an energy-consuming drying step, formulations of poorly soluble drugs can be obtained as granules instead of pellets, and formulations of poorly soluble drugs can be obtained in the absence of a costly pharmaceutical grade material such as microcrystalline cellulose.

In particular the present invention provides a solid formulation of florfenicol for oral administration, optionally together with animal feed, to warm-blooded animals such as cattle with naturally-occurring bovine respiratory disease, swine, sheep, goats and poultry. The present invention also provides a solid formulation of trimethoprim, optionally in combination with sulfadiazine (usually in a trimethoprim/sulfadiazine weight ratio of about 1:5), for oral administration to fish as an antibacterial agent effective against both gram-positive and gram-negative bacteria.

Thus, the present invention also provides a method of treatment of a warm-blooded animal comprising administration to said animal of an effective amount of a pharmaceutical granule composition comprising at least one drug (i) classifiable as Class II or Class IV of the Biopharmaceutical Classification System in an amount of no more than about 50% by weight of said pharmaceutical composition, a first excipient (ii) being a dextrin-containing compound in an amount from about 40 to about 85% by weight of said composition, and a second excipient (iii) comprising a solid fraction and optionally a liquid fraction, said second excipient (iii) being in an amount from about 10 to about 40% by weight of the composition and being selected from the group consisting of polyethylene glycols and polypropylene glycols having weight number molecular weights between about 300 and 10,000, glycerol, propylene glycol and glycerides. In particular drug (i) used in such a method may be florfenicol or trimethoprim.

The following examples are provided solely for the purpose of illustrating various embodiments of the invention, and without any intention of limiting the scope thereof.

EXAMPLE 1

Twin Screw Extruder for Producing a Pharmaceutical Granule Composition

Figure 3:
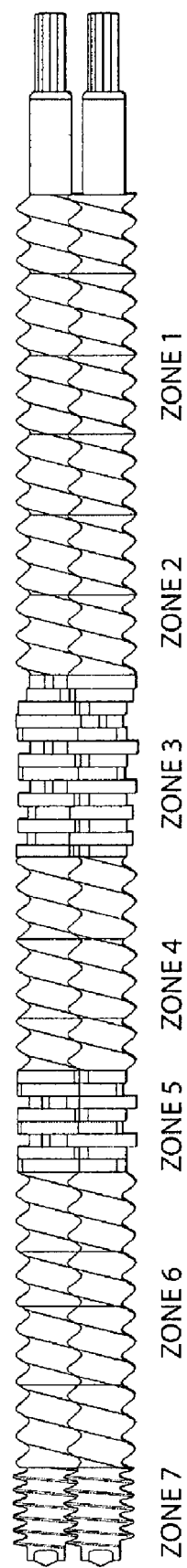
FIG. 3 shows a twin screw extruder useful for manufacturing granule compositions according to one embodiment of the present invention.

The twin screw extruder used for performing the following pharmaceutical granule preparations is described in FIG. 3. It consists of seven distinct zones, wherein zones (1), (2), (4) and (6) are three transport zones, zones (3) and (5) are two mixing zones and zone (7) is a densification zone (which could alternatively be omitted, if desired). The extruder is placed within a granulation chamber provided with'inlets for supplying the drug and the various excipients.

EXAMPLES 2 AND 3

Pharmaceutical Granule Formulations Including a Malto-Dextrin and Xanthan Gum

The following formulations were prepared using the extruding equipment of example 1:

| | |
|---|---|
| Low water-soluble drug: | 100 g |
| Polyethyleneglycol 400: | 52.5 g |
| Polyethyleneglycol 4000: | 187.5 g |
| Maltodextrin 01982 | 622.5 g |
| Xanthan gum: | 37.5 g |

Maltodextrin 01982 is a neutral taste, medium DE maltodextrin with good dispersibility which complies with European and U.S. Pharmacopeia and which is commercially available from Cerestar (Neuilly-sur-Seine, France). The solid fraction of the formulation consisting of hydrochlorothiazide (example 2), PEG 4000, maltodextrin and xanthan gum was homogenised in a planetary mixer. This mixture was fed into the twin screw extruder at a rate of 29.9 g/min. The liquid phase (PEG400) was continuously pumped into the twin screw extruder at a rate of 6.9 g/min. The screw speed during the extrusion was 250 rpm. The temperature of the different zones of the twin screw extruder was set at 25° C., yielding experimental extrusion temperatures of 25° C. in zone (1), 26° C. in zone (2), 26° C. in zone (3) and 25° C. in zones (4) and (5).

In the case of florfenicol (example 3) being used as the drug instead of hydrochlorothiazide, the same parameters were used and the experimental temperatures measured in zones (1) to (5) were 26° C., 28° C., 28° C., 27° C. and 25° C. respectively.

Figure 2:
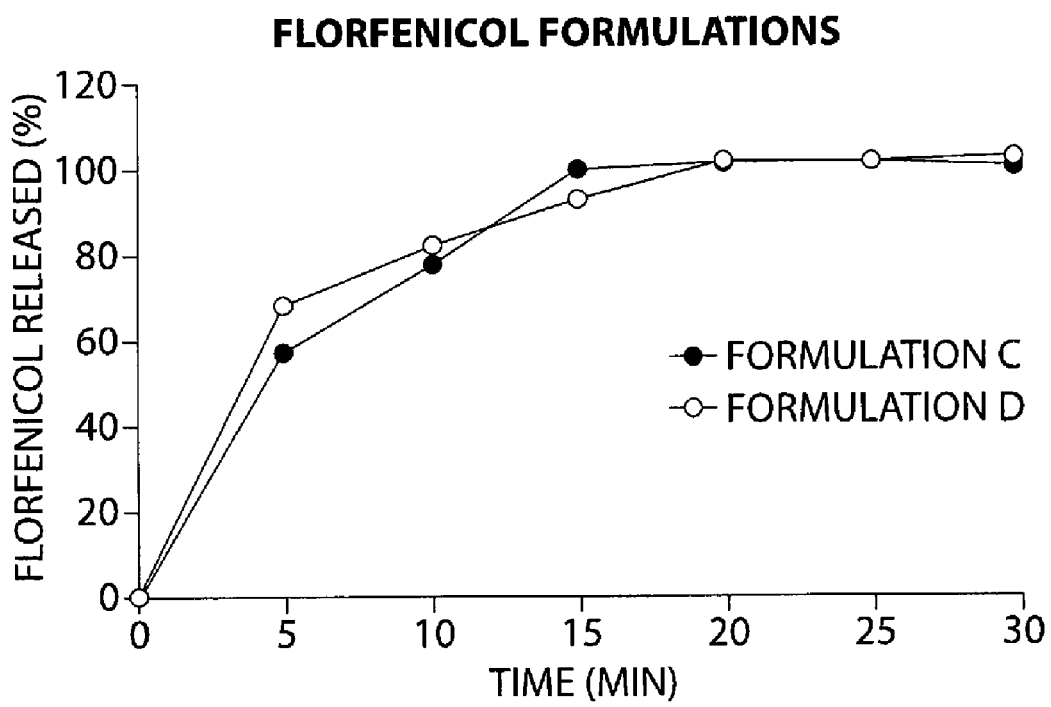
FIG. 2 represents the release, as a function of time, of florfenicol from a granule composition according to one embodiment of the invention.

The extruded granules were collected, sieved and further analysed for drug dissolution (data shown in FIGS. 1 and 2, formulations B and D). The dissolution test was performed at room temperature by using paddles rotating at 100 rpm, the dissolution medium being demineralized water. FIG. 1 shows that 72% release of hydrochlorothiazide (example 2) is obtained after 10 minutes, and 90% after 25 minutes. FIG. 2 shows that 80% release of florfenicol (example 3) is already obtained after 10 minutes, and 100% after 20 minutes.

EXAMPLES 4 AND 5

Pharmaceutical Granule Formulations Including Micro-Crystalline Cellulose

The following formulations were prepared using the extruding equipment of example 1:

| | |
|---|---|
| Low water-soluble drug: | 100 g |
| Polyethyleneglycol 400: | 52.5 g |
| Polyethyleneglycol 4000: | 250 g |
| Avicel PH 101: | 298.75 g |
| Avicel CL611: | 298.75 g |

The solid fraction of the formulation consisting of hydrochlorothiazide (example 4), PEG 4000, Avicel PH 101/Avicel CL 611 (commercially available from FMC Corporation, Philadelphia, Pa.) was homogenised in a planetary mixer. The homogeneous mixture was then fed into the twin screw extruder at a rate of 27.6 g/min. The liquid phase (PEG 400) was continuously pumped into the twin screw extruder at a rate of 9.2 g/minute. The screw speed during the extrusion was 250 rpm. The temperature of the different zones of the twin screw extruder was set at 25° C. yielding experimental temperatures of 25° C., 28° C., 27° C., 26° C. and 25° C. in zones 1 to 5, respectively.

In the case of florfenicol (example 5) being used as a drug instead of hydrochlorothiazide, the same parameters were used and the experimental temperatures measured were 25° C., 26° C., 27° C., 27° C. and 28° C. for the zones (1) to (5) respectively.

The extruded granules were collected, sieved and further analysed for drug dissolution (data shown in FIGS. 1 and 2, formulations A and C), using the same dissolution test method as in examples 2 and 3. FIG. 1 shows that 100% release of hydrochlorothiazide (example 4) is obtained after 10 minutes. FIG. 2 shows that 78% release of florfenicol (example 5) is already obtained after 10 minutes, and 100% after 15 minutes.

EXAMPLE 6

Comparative—Pharmaceutical Pellet Formulation

A pharmaceutical pellet formulation was made according to the extrusion-spheronisation process as disclosed in the examples of U.S. Pat. No. 6,368,634, but starting from the following composition (by weight):

| | |
|---|---|
| Florfenicol: | 20% |
| Polyethyleneglycol 400: | 21% |
| Avicel PH 101: | 59% |

Figure 4:
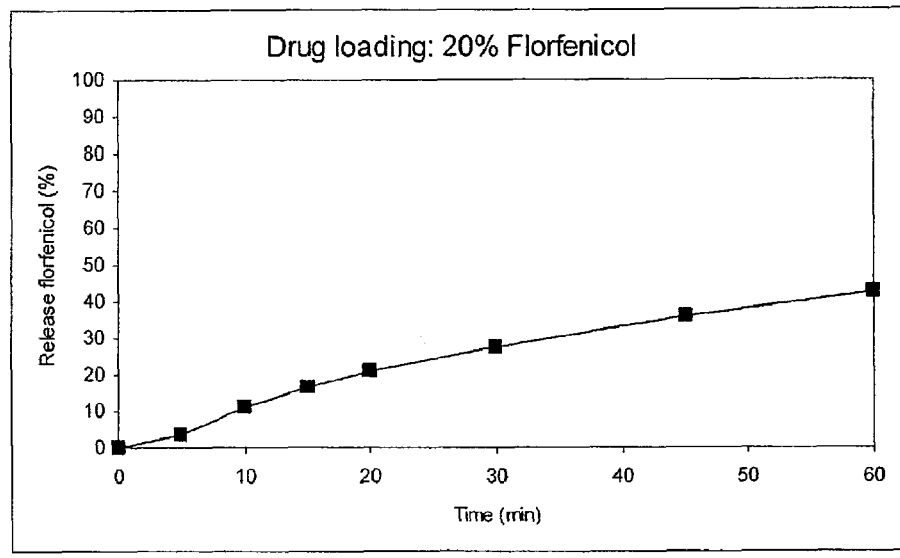
FIG. 4 shows the release, as a function of time, of florfenicol from a pellet composition according to the prior art.

The release rate of florfenicol from these pellets was determined as in the previous examples and, as shown in FIG. 4, was found to be quite slow: only 11% and 43% of the drug were dissolved after 10 minutes and after 60 minutes, respectively.

EXAMPLE 7

Pharmacokinetics of Florfenicol Granule Formulations in Broiler Chickens

The effect of a bolus oral administration of a florfenicol granule formulation according to the invention in fasted and non-fasted broiler chickens (average weight 2-3 kgs) was compared to the effect of a bolus intravenous administration of an injectable florfenicol formulation in the same animals. In both cases, the dosage used was 30 mg/kg.

The comparative formulation used for intravenous administration was Nuflor®, a commercially available injectable preparation with a drug concentration of 300 mg/ml.

The granule formulation used for oral administration was prepared according to the procedure of examples 2 and 3, except that the florfenicol content was 20% by weight of the formulation and the maltodextrin content was reduced accordingly.

Blood samples were taken from broilers at the following times after administration: 0.25 h, 0.5 h, 0.75 h, 1 h, 1.5 h, 2 h, 3 h, 4 h, 6 h, 8 h and 12 hours, respectively. Plasma analysis was performed by high performance liquid chromatography (HPLC) with UV detection with chloramphenicol as internal standard.

Figure 5:
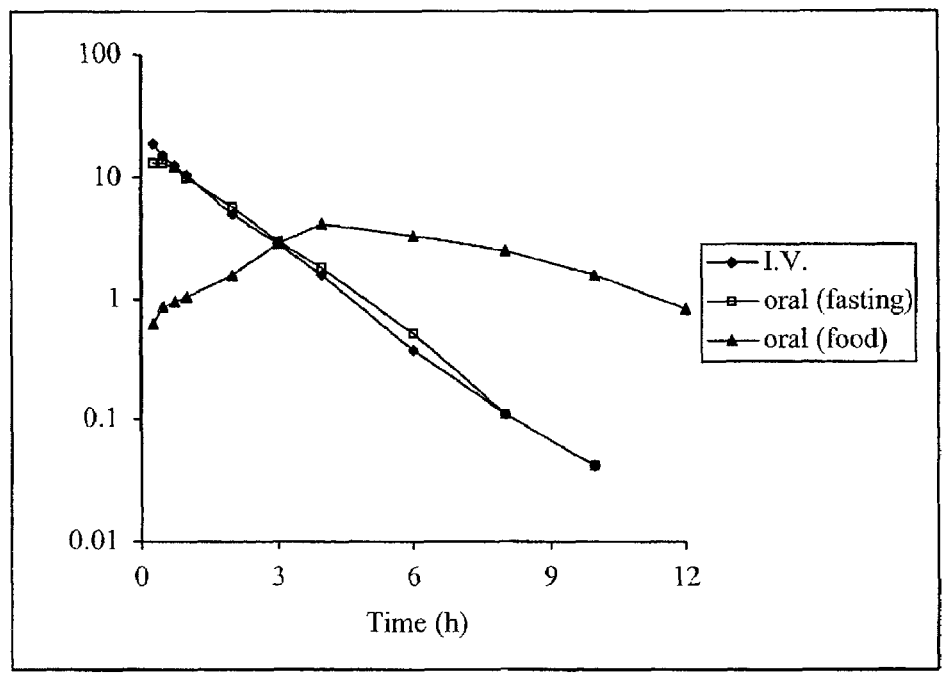
FIG. 5 shows florfenicol plasma concentrations in chickens after administration of a bolus dose of a florfenicol granule composition according to one embodiment of the invention, compared to intravenous administration of the same dose.

Results of mean plasma florfenicol concentrations (expressed in μg/ml) in chickens as a function of time are shown in FIG. 5.

EXAMPLE 8

Pharmacokinetics of Florfenicol Granule Formulations in Pigs

The effect of a bolus oral administration of a florfenicol granule formulation according to the invention in fasted and non-fasted pigs (average weight 20-35 kgs) was compared to the effect of a bolus intravenous administration of an injectable florfenicol formulation in the same animals. In both cases, the dosage used was 15 mg/kg.

The comparative formulation used for intravenous administration was Nuflor®, a commercially available injectable preparation with a drug concentration of 300 mg/ml.

The granule formulation used for oral administration was prepared according to the procedure of examples 2 and 3, except that the florfenicol content was 20% by weight of the formulation and the maltodextrin content was reduced accordingly.

Blood samples were taken from pigs at the following times after administration: 0.33 h, 0.66 h, 1 h, 1.5 h, 2 h, 3 h, 4 h, 6 h, 8 h, 12 h, 24 h and 30 hours, respectively. Plasma analysis was performed by high performance liquid chromatography (HPLC) with UV detection with chloramphenicol as internal standard.

Figure 6:
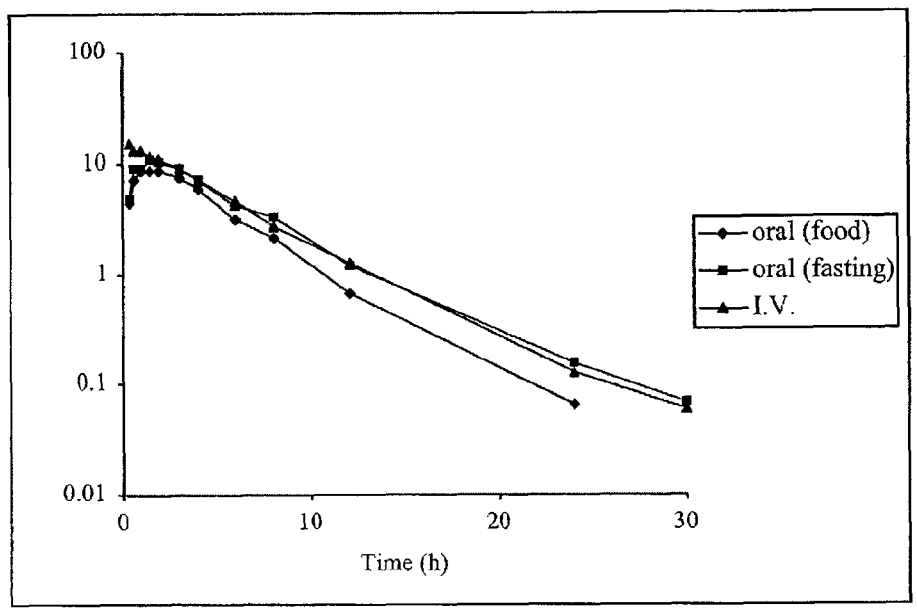
FIG. 6 shows florfenicol plasma concentrations in pigs after administration of a bolus dose of a florfenicol granule composition according to one embodiment of the invention, compared to intravenous administration of the same dose.

Results of mean plasma florfenicol concentrations (expressed in μg/ml) in pigs as a function of time are shown in FIG. 6.

EXAMPLE 9

Plasma Florfenicol Concentrations in Chickens after Continuous Administration of Granules, as Compared to Pellets, Together with Drinking Water The effect of a continuous oral administration, together with drinking water, of florfenicol solid formulations in broiler chickens (average weight 1.2-1.6 kg) was investigated. Comparison was made between the granule florfenicol formulation of example 7 (this invention) and the pellet florfenicol formulation of example 6 (i.e. according to U.S. Pat. No. 6,368,634), both having a florfenicol content of 20% by weight, in the same animals. In both cases, the dosage used was 30 mg florfenicol per kg of the animal, or 140 mg/L in drinking water, and administration was continued for 2 days.

Blood samples were taken from broilers at regular intervals, 4 times daily, after administration of said formulations. Plasma analysis was performed by high performance liquid chromatography (HPLC) with UV detection with chlor-amphenicol as internal standard.

Figure 7:
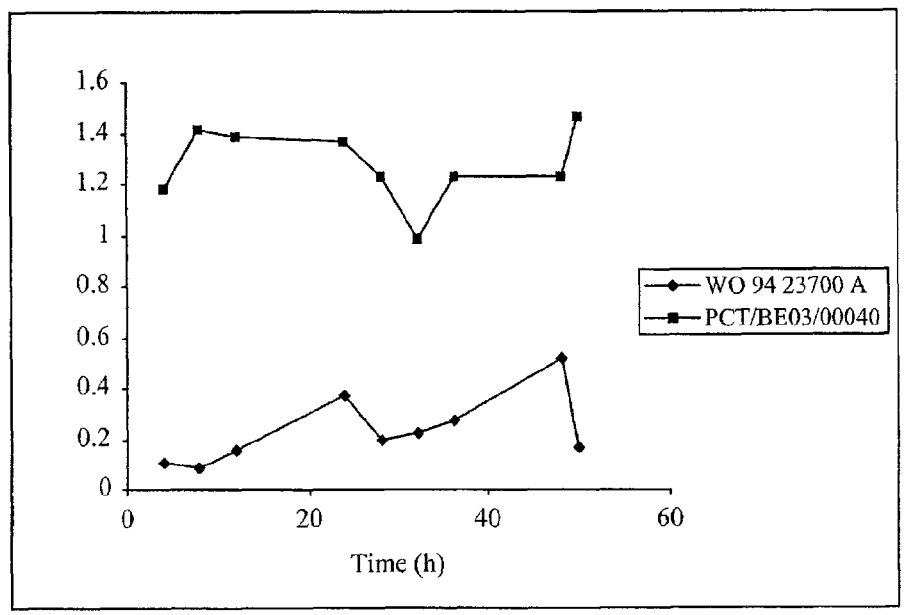
FIG. 7 shows florfenicol plasma concentrations in chickens, as a function of time, after continuous administration of a florfenicol granule composition according to one embodiment of the invention, compared to a florfenicol pellet composition of the prior art.

Results of mean plasma florfenicol concentrations (expressed in μg/ml) in broiler chickens as a function of time are presented in the following table and shown in FIG. 7 (wherein WO 94/23700 corresponds to U.S. Pat. No. 6,368,634, and PCT/BE03/00040 refers to this invention). It is quite surprising that the mean plasma concentration of florfenicol in chickens was continuously more than 2.3 times higher with the granule formulation of this invention than with the pellet formulation of the prior art, over the whole 48 hours period of the study. It is more particularly surprising that the mean plasma concentration of florfenicol in chickens remained more than 9 times higher with the granule formulation of this invention than with the pellet formulation of the prior art over the 12 hours period following the first day administration, and remained more than 4.4 times higher with the granule formulation of this invention than with the pellet formulation of the prior art over the 12 hours period following the second day administration. These facts are indicative of a significantly much more efficient treatment, at the same dosage, with this invention than according to the prior art formulation.

TABLE

| Time (hours) | Pellets (USP 6,368,634) | Granules (PCT/BE03/00040) |
|---|---|---|
| 4 | 0.11 | 1.18 |
| 8 | 0.09 | 1.41 |

TABLE-continued

| Time (hours) | Pellets (USP 6,368,634) | Granules (PCT/BE03/00040) |
|---|---|---|
| 12 | 0.15 | 1.38 |
| 24 | 0.38 | 1.36 |
| 28 | 0.19 | 1.23 |
| 32 | 0.22 | 0.98 |
| 36 | 0.28 | 1.23 |
| 48 | 0.52 | 1.23 |
| 50 | 0.17 | 1.46 |

EXAMPLE 10

Florfenicol High Drug Loading Formulation Including a Maltodextrin

The following formulation was prepared using the extruding equipment of example 1 and the extrusion conditions of examples 2 to 5:

| Florfenicol: | 300 g |
|---|---|
| Polyethyleneglycol 400: | 50 g |
| Polyethyleneglycol 4000: | 200 g |
| Maltodextrin 01983: | 410 g |
| Tween ® 80: | 40 g |

Tween® 80 used in this formulation is a well known commercially available non-ionic surface-active agent with emulsifying and fluidifying properties also designated as polysorbate 80 or polyoxyethylene 20 sorbitan monooleate.

Figure 8:
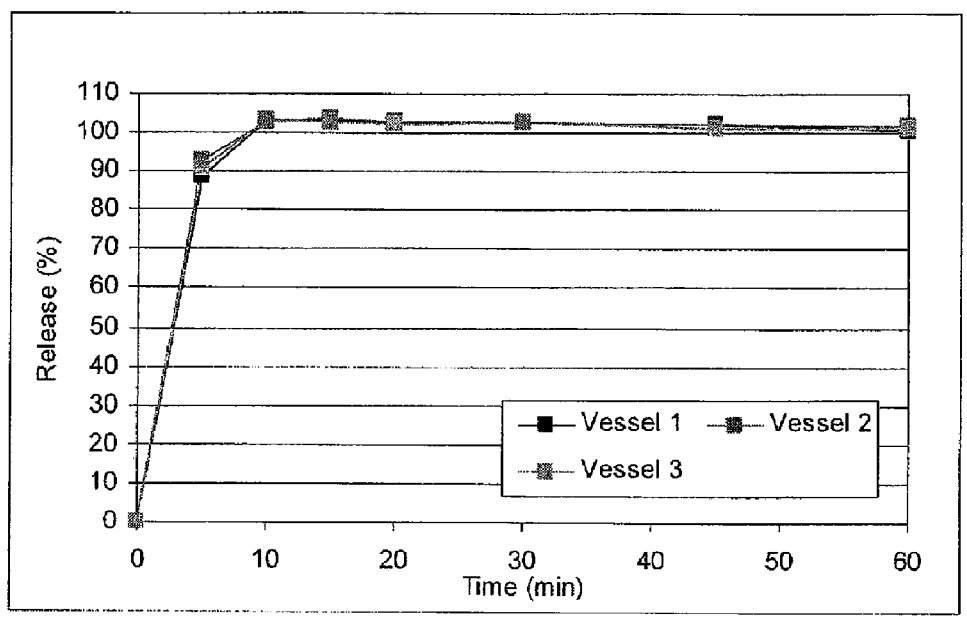
FIG. 8 shows the release, as a function of time, of florfenicol from a high drug content granule composition according to one embodiment of the invention.

Three batches of extruded granules were collected in three vessels 1 to 3, then sieved and further analysed for drug dissolution (data shown in FIG. 8, i.e. release profiles over a period of time ranging from 5 to 60 minutes) using the same dissolution test method as in examples 2 to 5. FIG. 8 shows a very good reproducibility of the dissolution profiles from the three different batches, with 90% florfenicol release after 5 minutes and 100% release after 10 minutes, i.e. a faster release than for the same drug at a lower drug loading (see example 3 and FIG. 2).

EXAMPLES 11 AND 12

Ketoprofen Formulations Including a Maltodextrin

The following formulations were prepared using the extruding equipment of example 1 and the extrusion conditions of examples 2 to 5:

| Ingredient | Example 11 | Example 12 |
|---|---|---|
| Ketoprofen | 100 g | 100 g |
| Polyethyleneglycol 400 | 50 g | nihil |
| Polyethyleneglycol 4000 | 200 g | 250 g |
| Tween 80 | 40 g | 40 g |
| Maltodextrin | 610 g | 610 g |

Figure 9:
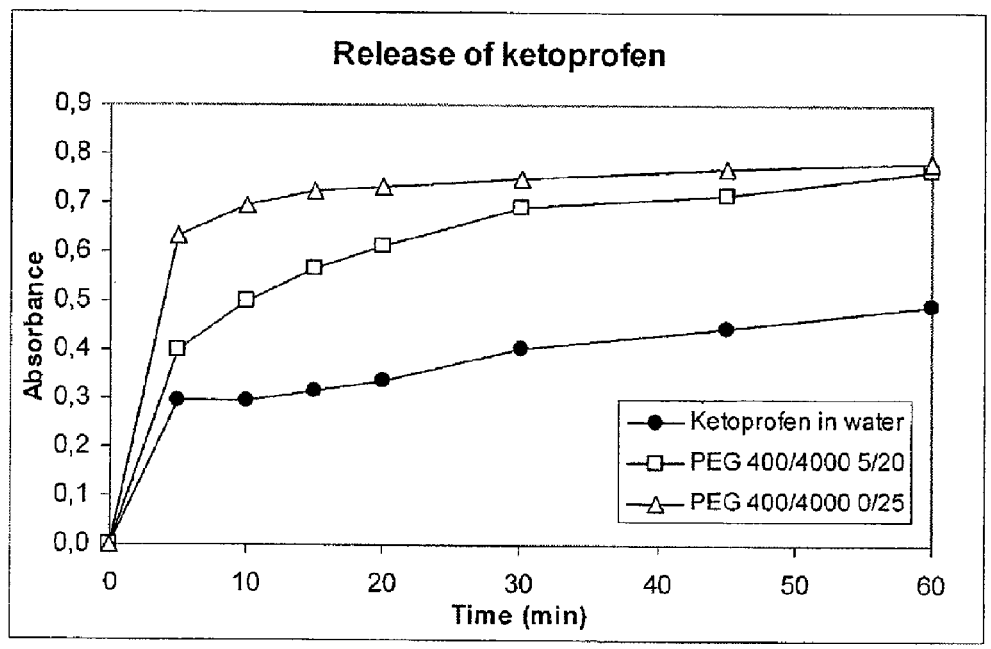
FIG. 9 shows the release, as a function of time, of ketoprofen from two different granule compositions according to the invention, as compared to ketoprofen release in water.

The ketoprofen release profiles of these formulations were determined by using the same dissolution test method as in examples 2 to 5 and were compared to ketoprofen release from water. FIG. 9 includes these release profiles over a period of time ranging from 5 to 60 minutes. FIG. 9 shows a ketoprofen release after 30 minutes of 70% and 75% for the formulations of example 11 and 12, respectively.

EXAMPLES 13 AND 14

Trimethoprim Formulations Including a Maltodextrin

The following formulations were prepared using the extruding equipment of example 1 and the extrusion conditions of examples 2 to 5:

| Ingredient | Example 13 | Example 14 |
|---|---|---|
| trimethoprim | 200 g | 200 g |
| Polyethyleneglycol 400 | 120 g | nihil |
| Polyethyleneglycol 4000 | 120 g | 240 g |
| surfactant | 40 g | 40 g |
| Maltodextrin 01983 | 520 g | 520 g |

In each set of formulations, the kind of surfactant was selected from the following list:
Tween® 80 (same as used in examples 10 to 12),
sodium lauryl sulfate,
Cremophor® RH40, and
Lutrol® F127.

Figure 10:
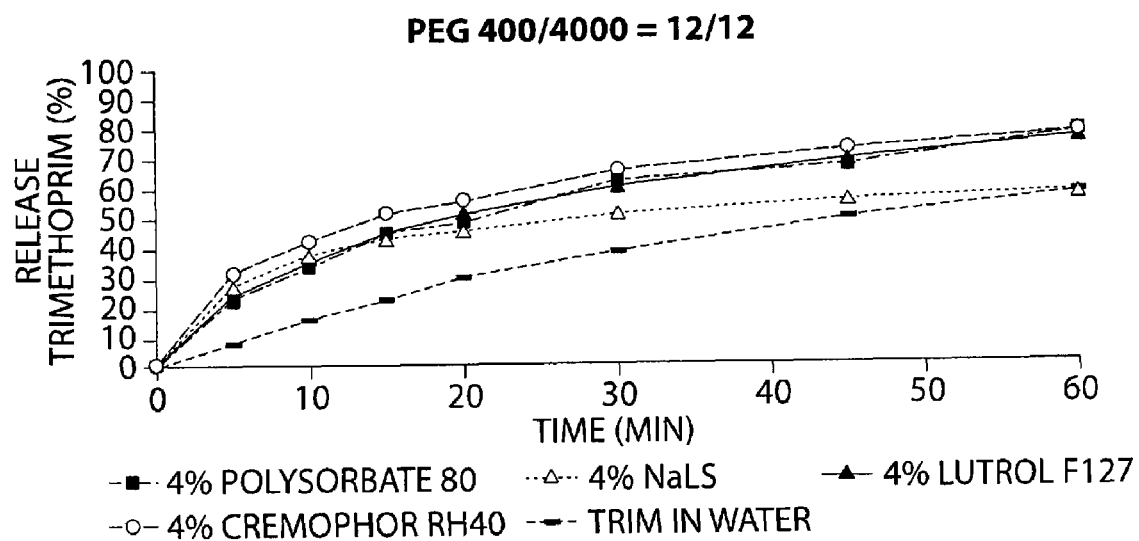
FIGS. 10 and 11 show the release, as a function of time, of trimethoprim from various granule compositions according to the invention, as compared to trimethoprim release in water.
Figure 11:
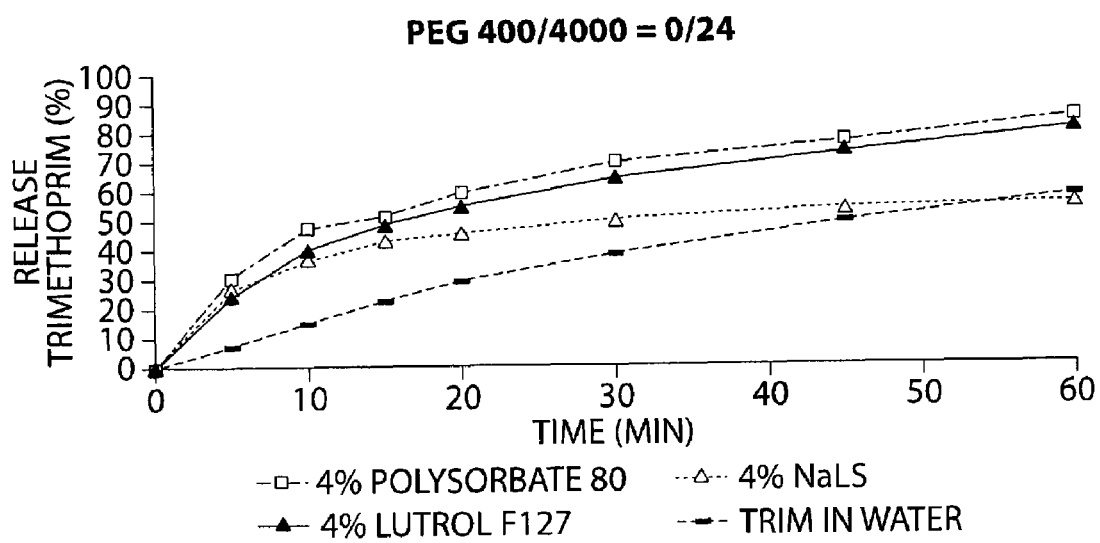

The trimethoprim release profiles of these formulations were determined by using the same dissolution test method as in examples 2 to 5 and 10 to 12, and were compared to trimethoprim release from water. FIGS. 10 and 11 include these release profiles over a period of time ranging from 5 to 60 minutes. FIG. 10 shows a trimethoprim release after 30 minutes ranging from 51% to 65% for the formulations of example 13, depending upon the kind of surfactant being present, as compared to a 38% trimethoprim release from water. FIG. 11 shows a trimethoprim release after 30 minutes ranging from 50% to 69% for the formulations of example 14, depending upon the kind of surfactant being present, as compared to a 38% trimethoprim release from water.

While the invention has been described in connection with specific embodiments thereof, it will be understood that it is capable of further modifications and this application is intended to cover variations, uses, or adaptations of the invention and including such departures from the present disclosure as come within the art to which the invention pertains and as may be applied to the essential features hereinbefore set forth as follows in the scope of the appended claims.

What is claimed is:

1. An oral pharmaceutical or veterinary granule composition in the form of a mixture consisting essentially of:
   (i) florfenicol constituting from above 20% to 50% by weight of the composition, said pharmaceutical or veterinary granule composition providing a florfenicol release of at least 80% within 10 minutes in water,
   (ii) a first excipient being a maltodextrin representing from 40% by weight to 85% by weight of said composition,
   (iii) a wetting amount of a second excipient being a polyethylene glycol having a weight number molecular weight between 300 and 5,000, said second excipient comprising a solid fraction and a liquid fraction, and representing from 15% to 40% by weight of said composition, and optionally one or more pharma-ceutically acceptable fillers selected from the group consisting of hydrocolloids, glidants, lubricants, surfactants and diluents, wherein the weight ratio of said first excipient (ii) to said second excipient (iii) is in a range from 1:1 to 5:1.

2. An oral pharmaceutical or veterinary granule composition according to claim 1, wherein said granules have a diameter ranging from 100 and 2,500 μm.

3. A composition comprising an oral veterinary granule composition according to claim 1, and drinking water.

4. A continuous process for manufacturing an oral pharmaceutical or veterinary granule composition in the form of a mixture consisting essentially of:
  (i) from above 20% to 50% by weight florfenicol,
  (ii) a first excipient being a maltodextrin representing from 40% by weight to 85% by weight of said composition, and
  (iii) a wetting amount of a second excipient being a polyethylene glycol having a weight number molecular weight between 300 and 5,000, said second excipient comprising a solid fraction and a liquid fraction, and representing from 15% to 40% by weight of said composition, wherein the weight ratio of said first excipient (ii) to said second excipient (iii) is in a range from 1:1 to 5:1, said continuous process comprising the steps of:
  (a) homogenising a mixture comprising said florfenicol (i), said first excipient (ii) and the solid fraction of said second excipient (iii),
  (b) feeding the mixture obtained in step (a) and the liquid fraction of said second excipient (iii) into an extruding means having one or more mixing zones and one or more transport zones, and
  (c) extruding the materials fed in step (b) while operating said extruding means at a temperature not above the melting temperature of the solid fraction of the second excipient (iii) until a pharmaceutical or veterinary granule composition providing a florfenicol release of at least 80% within 10 minutes in water is obtained.

5. A process according to claim 4, wherein said extruding means is a twin screw extruder.

6. A process according to claim 4, wherein said extruding means is operated at a temperature not above 60° C.

7. An oral pharmaceutical or veterinary granule composition according to claim 1, providing a florfenicol release of 100% within 10 minutes in water.

* * * * *